United States Patent [19]

Katada et al.

[11] Patent Number: 5,080,889
[45] Date of Patent: Jan. 14, 1992

[54] DIACYLGLYCERIN AND COSMETIC COMPOSITION

[75] Inventors: Masahiro Katada; Kenji Masui; Hisao Oomura; Yukitaka Tanaka, all of Ibaraki; Mitsuo Kondo; Takashi Komori, both of Chiba, all of Japan

[73] Assignee: Kao Corporation, Tokyo, Japan

[21] Appl. No.: 494,405

[22] Filed: Mar. 16, 1990

[30] Foreign Application Priority Data

Apr. 7, 1989 [JP] Japan .................. 1-89139
Apr. 11, 1989 [JP] Japan .................. 1-91502

[51] Int. Cl.$^5$ ............................. A61K 7/021
[52] U.S. Cl. ........................ 424/63; 424/59; 424/70; 424/64; 514/784; 514/785; 514/786; 514/873; 514/937; 514/938; 514/939; 514/943
[58] Field of Search ............ 424/63, 64, 59, 70; 514/784, 785, 786, 873, 937, 938, 939, 943

[56] References Cited

U.S. PATENT DOCUMENTS 4,126,702  10/1978  Vanlerberghe et al. ........... 424/63

FOREIGN PATENT DOCUMENTS 0319126  9/1988  European Pat. Off.
2535778  2/1976  Fed. Rep. of Germany.
275221   8/1988  Japan.

OTHER PUBLICATIONS

Grant and Hackh's Chemical Dictionary, 5th ed., pp. 173, 406.

*Primary Examiner*—Thurman K. Page
*Assistant Examiner*—William E. Benston, Jr.
*Attorney, Agent, or Firm*—Birch, Stewart, Kolasch & Birch

[57] ABSTRACT

The following diacylglycerin is useful for a cosmetic oil and a cosmetic composition such as pack, cream and emulsion.

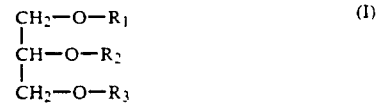

(where one each of $R_1$, $R_2$, and $R_3$ denotes a residue of a straight-chain saturated fatty acid having 11-17 carbon atoms, a residue of a branched-chain saturated fatty acid having 10-18 carbon atoms, and a hydrogen atom).

6 Claims, No Drawings

DIACYLGLYCERIN AND COSMETIC COMPOSITION

FIELD OF INDUSTRIAL APPLICATION

The present invention relate to a liquid oil preparation consisting of a new diacylglycerin. More particularly, it is concerned with a liquid oil preparation which is liquid at room temperature, highly stable to oxidation and decomposition, gives a good feel to the skin, and permits formulation in high concentrations.

PRIOR ART

Acylglycerins include monoacyl-, diacyl-, and triacylglycerin. Monoacylglycerin is used as a surface active agent. Triacrylglycerin is used in a broad range of applications as oils and fats (represented by natural oils and fats) and also as oil preparations. By contrast, diacylglycerin is regarded as an impurity which has an adverse effect on the surface active performance of monoacylglycerin and lowers the crystallinity of triacylglycerin.

However, diacylglycerin per se is considered to be an oil preparation having a slight polarity owing to one hydroxyl group it possesses in its molecule. The use of diacylglycerin as a base for cosmetics and drugs is disclosed in Japanese Patent Laid-open Nos. 44040/1979 and 166108/1981. On the other hand, there are several commercial diacylglycerins having a single acyl residue, such as distearoyl glycerin and dioleyl glycerin. Because of their safety, stability, and good feel, they are expected to replace the conventional oil bases such as paraffins, waxes, higher alcohols, and olive oil which are used in the cosmetic field.

Although diacylglycerin has the feature of an oil preparation with polarity, it is used mainly as a crystalline base having a high melting point. It has never attracted attention as an oil preparation for cosmetics. It is possible to lower the melting point of diacylglycerin by the introduction of an unsaturated acyl group or a short-chain acyl group. However, the former deteriorates the stability to autoxidation, and the latter makes diacylglycerin liable to decomposition and poses a problem associated with irritation and safety. Therefore, for diacylglycerin to be used as a liquid oil preparation, a special device has to be made. For this reason, diacylglycerin has been limited in usage and application areas.

A liquid oil shields hairs to increase their water content, or acts directly on the horny layer to increase its flexibility. Unfortunately, a liquid oil is usually sticky and glossy with a poor feel if it produces a great shielding effect. By contrast, a liquid oil which is not sticky and glossy is poor in flexibilizing effect and is often irritating. In order to eliminate these disadvantages, a liquid oil is applied to the skin and hairs in the form of an emulsified cosmetic, especially water-in-oil type emulsion.

The diacylglycerin having the formula (I) in which the residue of a straight-chain saturated fatty acid has 14 carbon atoms and the residue of a branched-chain saturated fatty acid is shown by the formulae (i) to (iii) is disclosed in JP-A 1-106846 published on Apr. 24, 1989, corresponding to U.S. Ser. No. 246 875 filed on Sep. 20, 1988 and EP-A 319 126 published on June 7, 1989.

SUMMARY OF THE INVENTION

With the foregoing in mind, the present inventors studied diacylglycerin combined with a different kind of acyl group, and evaluated the performance of such diacylglycerin as a liquid oil preparation. As the result, it was found that diacylglycerin having the residue of a specific branched-chain saturated fatty acid and the residue of a specific straight-chain saturated fatty acid in the molecule is liquid at room temperature, has good stability to oxidation and high resistance to decomposition, gives a good feel to the skin, and permits formulation in high concentrations. The present invention was completed on the basis of this finding.

The invention provides a new diacylglycerin having the formula (I):

(where one each of $R_1$, $R_2$, and $R_3$ denotes a residue of a straight-chain saturated fatty acid having 11-17 carbon atoms, and (6) a residue of a branched-chain saturated fatty acid having 10-18 carbon atoms, and the third of $R_1$, $R_2$ and $R_3$ is hydrogen atom, provided that the ones are excluded in which the residue of a straight-chain saturated fatty acid has 14 carbon atoms and the residue of a branched-chain saturated fatty acid is represented by the formulas (i) to (iii) below.)

(i) Residue of methyl-branched isostearic acid represented by the formula below.

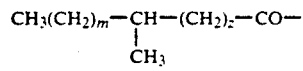

(where m and n each are integers of 4 to 10, $m+n=14$, distributed with the center at $m=n=7$.)

(ii) Residue of 5,7,7-trimethyl-2-(1,3,3-trimethylbutyl)-octanoic acid.

(iii) Residue of 2-heptylundecanoic acid.

The invention further provides a liquid oil composition comprising (A) the diacylglycerin (I) defined above and (B) another oil liquid.

The invention further relates to a liquid cosmetic composition comprising (A) the diacylglycerin having formula (I'), (B) a lower alcohol and (C) water.

(where one each of $R_1$, $R_2$, and $R_3$ denotes a residue of a straight-chain saturated fatty acid having 11-17 carbon atoms, a residue of a branched-chain saturated fatty acid having 10-18 carbon atoms, and a hydrogen atom.)

The invention moreover provides a cosmetic pack composition comprising (A) the diacylglycerin having the formula (I') and (B) a carrier, an oily solid cosmetic composition comprising (A) the diacylglycerin having the formula (I') and (B) a hydrocarbon wax and an emulsion cosmetic composition comprising (A) the diacylglycerin having the formula (I'), (B) a surfactant and (C) water.

DETAILED DESCRIPTION OF THE INVENTION

The diacylglycerin of the present invention contains the residue of a straight-chain saturated fatty acid having 11-17 carbon atoms, whose examples include undecanoic acid, dodecanoic acid, tridecanoic acid, tetradecanoic acid, pentadecanoic acid, hexadecanoic acid, and heptadecanoic acid. With the residue having 10 or less carbon atoms, the diacylglycerin undergoes hydrolysis so easily that it is not suitable for use as an oil preparation. With the residue having 18 or more carbon atoms, the diacylglycerin has such a high freezing point that it is not suitable for use as an oil preparation.

The diacylglycerin of the present invention contains the residue of a branched-chain saturated fatty acid having 10-18 carbon atoms, whose examples include dimethyloctanoic acid, trimethylheptanoic acid, butylmethylhexanoic acid, ethylmethylnonanoic acid, propylmethylnonanoic acid, trimethyldecanoic acid, pentylmethyloctanoic acid, butylmethylnonanoic acid, propyldodecanoic acid, pentyldecanoic acid, hexyldecanoic acid, butylpentylheptanoic acid, hexyldodecanoic acid, pentylundecanoic acid, 7-methyl-2-(3-methylhexyl)decanoic acid, 7-methyl-2-(3-methylbutyl)octanoic acid, and 5,7,7-trimethyl-2-(1,3,3-trimethylbutyl)octanoic acid. Additional examples which are commercially available from Nissan Chemical Industries, Ltd. include isodecanoic acid, isotridecanoic acid, isomyristic acid, isopalmitic acid, and isostearic acid.

The diacylglycerin of the present invention may be produced from the above-mentioned branched-chain saturated fatty acid and straight-chain saturated fatty acid and glycerin by the process used for the production of ordinary acylglycerin. The process involves the steps of mixing the above-mentioned branched-chain saturated fatty acid and straight-chain saturated fatty acid and glycerin in equimolar amounts, heating them at 200°-230° C. with the elimination of water formed under reduced pressure, thereby yielding a mixture of acylglycerins, and subjecting the mixture to distillation or column chromatography, thereby separating the fraction of diacylglycerin. The thus obtained diacylglycerin is a random mixture containing a diacylglycerin composed only of the residue of a branched-chain saturated fatty acid, a diacylglycerin composed of the residue of a branched-chain saturated fatty acid and the residue of a straight-chain fatty acid, and a diacylglycerin composed only of the residue of a straight-chain saturated fatty acid. The desired diacylglycerin of the present invention may be obtained from the mixture by utilizing their difference in melting point or by recrystallization from a proper solvent such as hexane.

There is another advantageous process, which involves the steps of converting either of the branched-chain saturated fatty acid or straight-chain saturated fatty acid into a highly reactive derivative, and then esterifying the derivative. An example of the highly reactive derivative is an acid halide of a fatty acid. A preferred example of the process which involves an acid halide is carried out as follows: One mol of a branched-chain saturated fatty acid (as the starting material) is reacted with 1-5 mol, preferably 1-2 mol of a halogenating agent such as thionyl chloride, thionyl bromide, and phosphorus trichloride, at 0°-100° C., preferably 20°-80° C., to give an acid halide. One mol of a straight-chain saturated fatty acid is reacted with 1 mol of glycerin with heating at 200°-230 C., with the elimination of water formed under reduced pressure, to give an acylglycerin of the straight-chain saturated fatty acid. This product is subjected to molecular distillation to give a monoacylglycerin of a straight-chain saturated fatty acid. Subsequently, 1 mol of the branched-chain saturated fatty acid halide is reacted with 0.5-3 mol, preferably 1-1.5 mol, of the monoacylglycerin of a straight-chain saturated fatty acid by the aid of a dehydrohalogenating agent such as pyridine and quinoline in an amount of 1-3 mol, preferably 1-1.5 mol, for the acid halide. This reaction is carried out in an inert solvent such as benzene, toluene, xylene, and hexane in an amount of 1-10 times, preferably 3-5 times, the volume of the acid halide, with stirring and heating at 50°-100° C., preferably 60°-80° C. After the removal of amine hydrohalide formed, the acylglycerin undergoes molecular distillation or column chromatography to give the desired diacylglycerin containing the residue of a branched-chain saturated fatty acid and the residue of a straight-chain saturated fatty acid.

There is further another advantageous process for producing the desired product by using lipase without going through a highly reactive derivative. According to this process, 1 mol of a branched-chain saturated fatty acid is reacted with 1 mol of glycerin at 200°-230° C., with the elimination of water formed under reduced pressure, to give an acylglycerin having the residue of the branched-chain saturated fatty acid. This acylglycerin undergoes molecular distillation to give a monoacylglycerin having the residue of the branched-chain saturated fatty acid. This monoacylglycerin is mixed with a straight-chain saturated fatty acid in equimolar amount. They undergo esterification reaction by the aid of lipase as a catalyst to give a diacylglycerin containing the residue of a branched-chain saturated fatty acid and the residue of a straight-chain saturated fatty acid. The resulting product undergoes molecular distillation as the post-treatment according to the degree of esterification. For example, in the case where the degree of esterification of the straight-chain saturated fatty acid is low, it is necessary to remove the residual straight-chain fatty acid and monoacylglycerin. In addition, it is possible to remove triacylglycerin as a by-product by molecular distillation or column chromatography. This process may be carried out most effectively by using lipase having the α-position selectivity or lipase which is selective for partial glycerides.

Among the above-mentioned processes, the lipase process is most desirable from the standpoint of economy and the purity of resulting oil preparation. No matter what the process, the resulting oil preparation is a mixture of monoacylglycerin, diacylglycerin, and triacylglycerin. To achieve the object of the present invention, it is desirable that the oil preparation contain diacyl glycerine in an amount higher than 85 wt %, preferably higher than 90 wt %, and that this diacylglycerin contain the one represented by the formula (I) (in which either of the two acyl groups is the residue of a straight-chain saturated fatty acid having 11-17 carbon atoms and the other is the residue of a branched-chain saturated fatty acid having 10-18 carbon atoms) in an amount higher than 90 wt %.

By the above-mentioned process, there is obtained the diacylglycerin of the present invention which has the residue of a branched-chain saturated fatty acid and the residue of a straight-chain fatty acid. It has the following features, which make it suitable for use as a liquid oil preparation for cosmetics or external drugs to be applied directly to the skin.

(1) It is liquid at room temperature.

(2) It is chemically and thermally stable because the acyl group is the residue of a saturated fatty acid.

(3) It gives a good feel to the skin.

(4) It is highly miscible with both polar components and non-polar components, because it has a hydroxyl group in the molecule.

As mentioned above, the diacylglycerin of the present invention is liquid at room temperature and functions as a polar oil preparation which stabilizes emulsion systems. Therefore, it is easy to handle, without the need of heating and melting the solid component which crystallizes out at room temperature. Moreover, it does not cause phase separation due to crystallization even when incorporated into emulsion systems.

The diacylglycerin of the present invention may be used alone as an oil preparation of cosmetics or external drugs. It may also be incorporated into commonly known oil preparations, vaselin, liquid paraffin, and natural fats and oils.

The invention will below be illustrated in view of the diacylglycerin having the formula (I').

The liquid cosmetic of the present invention has a low degree of irritation to the skin and gives a good feel with reduced stickiness and glossiness.

The component [A]applies to the above shown explanation about the diacylglycerin having the formula (I). The oil preparation of the invention may contain diacylglycerin in an amount higher than 70 wt %, preferably higher than 80 wt %, and more preferably higher than 90 wt % and that this diacylglycerin contain the one represented by the formula (I) (in which either of the two acyl groups is the residue of a straight-chain saturated fatty acid having 11-17 carbon atoms and the other is the residue of a branched-chain saturated fatty acid having 10-18 carbon atoms) in an amount higher than 70 wt %, preferably higher than 80 wt %, and more preferably higher than 90 wt %.

The lower alcohol used as component (B) in the present invention is typically ethanol or propanol.

The three components (A), (B), and (C) used in the present invention should be mutually soluble to give a clear product. Therefore, the amount of diacylglyerin as component (A) should be 1-40 wt %, preferably 2-20 wt %; the amount of lower alcohol as component (B) should be 45-98 wt %, preferably 55-90 wt %; and the amount of water as component (C) should be 1-50 wt %, preferably 5-20 wt %.

If the liquid cosmetic of the present invention is to be applied to the skin, it may be incorporated with cold-feeling agents, anti-inflammatory agents, vitamins, hormones, and animal and vegetable extracts. For the application to hairs, it may be incorporated with an anti-scurf agent and hair tonic. In either cases, it may be incorporated with antioxidants, UV light absorbers, dyestuffs, perfumes, and humectants which are commonly for cosmetics.

The pack comsmetic composition comprises (A) the diacylglycerin (I') and a carrier such as a film-forming material or another material to form cream, paste, gelly and aerosol. It serves to maintain the moisture on the skin for long periods of time. It is preferable that the composition comprises 0.5 to 30 wt. %, more preferably 1 to 15 wt. %, of the diacylglycerin and the balance of the carrier and other conventional additives. A polyol, serving to maintain the moisture, may be mixed with the composition in an amount of 0.5 to 20 wt. %, preferably 1 to 10 wt. % or applied to the skin together with the composition. It includes propylene glycol, dipropylene glycol, 1,3-butanediol, polyethylene glycol, polypropylene glycol, hydroxypropyletherized glycolipid ester, disclosed in JP-B 57-47197. The carrier includes a film-forming material such as polyvinyl alcohol, carboxymethyl cellulose, a water-soluble salt of arginic acid, a polyacrylic ester, polyvinyl pyrrolidone, natural latex and polymer latex. It is used in an amount of 5 to 50 wt. %, preferably 10 to 25 wt. %. A filler to increase a viscosity may be used in the composition, such as hydroxyethylcellulose, carboxyvinyl polymer and bee gum, in an amount of 0.01 to 10 wt. %. A pigment may be used, such as titanium oxide, talc and caoline, in an amount of 5 to 20 wt. %. A paste of the invention may be produced by mixing 10 to 60 wt. % of a fat-absorbing powder, such as caoline, bengel, talc, zinc oxide and titanium oxide, well with the diacylglycerin and water according to the disclosure of JP-A 63-230612. Other additives may be used, such as a lubricant, a surfactant, a natural moisture-keeping material, an amino acid, a vitamine, an animal or vegetable essence, a UV absorbant, an antiseptic, a preservative, a chelating agent, an anti-oxidant, a coloring matter, a perfume and a pH adjuster.

The cosmetic solid composition comprises (A) the diacylglycerin (I') and (B) a hydrocarbon wax. (B) may be used in an amount of 0.01 to 10 wt. % based on (A). It is improved in view of feeling of touch on the skin, gloss and the moisture-keeping effect. It is used for a lip cream and a lipstick. The hydrocarbon wax includes, for example, solid paraffin, ceresin, microcrystalline wax and polyethylene wax having a molecular weight of 700 to 2,000. The composition may contain another liquid oil such as hydrocarbons, triglycerides, ester oils, silicone oils, diglycerides, alcohols and acids. The diacylglycerin may be used in an amount of 20 to 100 wt. %, preferably 30 to 90 wt. %, based on all the liquid oils used. The composition may further include another solidifying agent such as carnauaba wax, rice wax, wood wax, bee wax, candelila wax, sunflower wax, whale wax and montan wax. The (B) may be used in an amount of 50 to 100 wt. %, preferably 70 to 100 wt. %, based on all the solidifying agents. The same additives as shown in view of the pack composition may be used here.

The cosmetic emulsion composition comprises (A) the diacylglycerin, (B) a surfactant and (C) water. It is improved in view of feeling on touch, flexibility and clogging on the skin. The surfactant includes an anionic surfactant such as an alkyl sulfate, a salt of an aliphatic acid (soap) and an alkyl phosphate, a nonionic surfactant such as a polyoxyethylene alkyl ether, an alkyl ether of polyglycerin, an aliphatic ester, sorbitan ester of polyoxyethylene, saccharose ester of an aliphatic acid and an alkyl glycoside, a cationic surfactant and an amphoteric surfactant. The composition preferably comprises 0.1 to 80 wt. %, more preferably 1 to 20 wt. %, of (A), an emulsifying effective amount of (B), for example, 0.05 to 10 wt. %, more preferably 0.1 to 5 wt. %, and the balance, that is, 10 to 99 wt. %, of (C). A moisture-keeping agent may be used in an amount of 0.5 to 50 wt. %, more preferably 2 to 20 wt. %, such as propylene glycol, dipropylene glycol, 1,3-butylene glycol, sorbitol, polyethylene glycol, pyrrolidone and sodium carboxylate. The combination of (A) and 1,3-butylene glycol provides a synergetic effect to keep the moisture. Please see JP-A 63-185912. The micro emulsion is available, using 1 to 5 wt. % of (A), 1 to 15 wt. % of (B), 2 to 20 wt. % of a polyol being compatible with (A) and 40 to 96 wt. % of (C). The same additive as shown in the pack composition may be used here, too.

EXAMPLE 1

In a 2-liter reaction vessel equipped with a thermometer, nitrogen-introducing capillary, reflux condenser (with a water separating tube), and stirrer were placed 568 g (2.0 mol) of 7-methyl-2-(3-methylhexyl)decanoic acid, 184 g (2.0 mol) of purified glycerin, and 1.2 g of calcium hydroxide. The reactants underwent esterification at 230°-240° C. under a nitrogen stream. About 10 hours later, when water was not formed any longer, the reaction product underwent distillation under reduced pressure at 210°-220° C. and 15-25 mmHg for the removal of unreacted glycerin. When glycerin was distilled away almost completely, the reaction product underwent thin-film molecular distillation to give 225 g of a fraction having a boiling point of 170°-175° C. at 0.03-0.05 mmHg. This fraction was identified as a monoacylglycerin of 7-methyl-2-(3-methylhexyl)-deconoic acid. Hydroxyl number: 309.0

In a 2-liter reaction vessel equipped with a thermometer, reflux condenser, and stirrer were placed 358 g (1 mol) of monoacylglycerin of 7-methyl-2-(3-methylhexyl)decanoic acid, 274 g (1.2 mol) of tetradecanoic acid (myristic acid), and 80 g of commercial lipase preparation "Lipozyme 3A" (Mucor miehei-originated lipase immobilized on an anion-exchange resin, made by Novo Industry A.S.). The reactants underwent esterification reaction with stirring at 50°-C. for 5 hours under a reduced pressure of 100-300 mmHg. After the completion of the reaction, the lipase preparation was filtered out and the reaction product (filtrate) underwent thin-film molecular distillation at 190°-195° C. and 0.03-0.05 mmHg to remove excess myristic acid and unreacted monoacylglycerin. Thus there was obtained 548 g of the desired diacylglycerin containing the residues of 7-methyl-2-(3-methylhexyl)decanoic acid and myristic acid.

EXAMPLE 2

The same procedure as in Example 1 was performed on 302 g (1.0 mol) of monoacylglycerin of 7-methyl-2-(3-methylbutyl)octanoic acid and 274 g (1.2 mol) of myristic acid to give 492 g of diacylglycerin containing the residues of 7-methyl-2-(3-methylbutyl)octanoic acid and myristic acid.

EXAMPLE 3

The same procedure as in Example 1 was performed on 246 g (1.0 mol) of monoacylglycerin of isodecanoic acid (a mixture of diemthyloctanoic acid and trimethylheptanoic acid) and 274 g (1.2 mol) of myristic acid to give 367 g of diacylglycerin containing the residues of isodecanoic acid and myristic acid.

EXAMPLE 4

In a 2-liter reaction vessel equipped with a thermometer, reflux condenser, and stirrer were placed 356 g (1 mol) of monoacylglycerin of 5,7,7-trimethyl-2-(1,3,3-trimethylbutyl)octanoic acid, 240 g (1.2 mol) of dodecanoic acid, and 80 g of commercial lipase preparation "Lipozyme 3A" (Mucor miehei-originated lipase immobilized on an anion-exchange resin, made by Novo Industry A.S.). The reactants underwent esterification reaction with stirring at 50° C. for 5 hours under a reduced pressure of 100-300 mmHg. After the completion of the reaction, the lipase preparation was filtered out and the reaction product (filtrate) underwent thin-film molecular distillation at 190°-195° C. and 0.03-0.05 mmHg to remove excess dodecanoic acid and unreacted monoacylglycerin. Thus there was obtained 464 g of the desired diacylglycerin containing the residues of 5,7,7-trimethyl-2-(1,3,3-trimethylbutyl)octanoic acid and dodecanoic acid.

EXAMPLE 5

The same procedure as in Example 4 was performed on 356 g (1 mol) of monoacylglycerin of 5,7,7-trimethyl-2-(1,3,3-trimethylbutyl)octanoic acid and 307 g (1.2 mol) of hexadecanoic acid to give 521 g of diacylglycerin containing the residues of 5,7,7-trimethyl-2-(1,3,3-trimethylbutyl)octanoic acid and hexadecanoic acid.

COMPARATIVE EXAMPLE 1

In a 2-liter reaction vessel equipped with a thermometer, reflux condenser, and stirrer were placed 358 g (1 mol) of monoacylglycerin of 2-heptylundecanoic acid, 340 g (1.2 mol) of octadecanoic acid (stearic acid), and 80 g of commercial lipase preparation "Lipozyme 3A" (made by Novo Industry A.S.). The reactants underwent esterification reaction with stirring at 70° C. for 5 hours under a reduced pressure of 100-300 mmHg. After the completion of the reaction, the lipase preparation was filtered out and the reaction product (filtrate) underwent thin-film molecular distillation at 190°-195° C. and 0.03-0.05 mmHg to remove excess stearic acid and unreacted monoacylglycerin. Thus there was obtained 530 g of the desired diacylglycerin containing the residues of 2-heptylundecanoic acid and stearic acid.

COMPARATIVE EXAMPLE 2

In the same reaction vessel as used in Comparative Example 2 were placed 218 g (1 mol) of monoacylglycerin of 2-ethylhexanoic acid, 173 g (1.2 mol) of octanoic acid, and 80 g of commercial lipase preparation "Lipozyme 3A". The reactants underwent esterification reaction with stirring at 40° C. for 5 hours under a reduced pressure of 100-300 mmHg. After the completion of the reaction, the lipase preparation was filtered out and the reaction product (filtrate) underwent thin-film molecular distillation at 90°-100° C. and 0.05-0.07 mmHg to remove excess octanoic acid and unreacted monoacylglycerin. Thus there was obtained 265 g of the desired diacylglycerin containing the residues of 2-ethylhexanoic acid and octanoic acid.

The diacylglycerins obtained in Examples 1 to 5 and Comparative Examples 1 and 2 have the composition, viscosity, and freezing point as shown in Table 1.

EXAMPLE 6

The same procedure as in Example 5 was carried out except that the hexadecanoic acid was replaced by 274 g (1.2 mol) of tetradecanoic acid to give 506 g of diacylglycerin containing the residues of 5,7,7-trimethyl-2-(1,3,3-trimethylbutyl)octanoic acid and tetradecanoic acid.

The diacylglycerins obtained in Examples 1 to 6 have the purity and physical properties as shown in Table 1.

TABLE 1

| Example No. | Constituting residue of fatty acid Branched-chain fatty acid | Straight-chain fatty acid | Content of diacylglycern (wt %) | Composition of diacylglycerin (wt %) Branched chain to branched chain | Branched chain to straight chain | Straight chain to straight chain | Viscosity (cps) at 25° C. | Freezing point (°C.) |
|---|---|---|---|---|---|---|---|---|
| 1 | 7-methyl-2-(3-methylhexyl)-decanoic acid | Tetradecanoic acid | 94.4 | 4.1 | 95.7 | 0.2 | 141 | below −20 |
| 2 | 7-methyl-2-(3-methylbutyl)-octanoic acid | Tetradecanoic acid | 95.8 | 8.2 | 91.7 | 0.1 | 104 | −17.3 |
| 3 | Isodecanoic acid | Tetradecanoic acid | 89.1 | 9.8 | 90.1 | 0.1 | 77 | −12.0 |
| 4 | 5,7,7-trimethyl-2-(1,3,3-trimethylbutyl)octanoic acid | Dodecanoic acid | 97.1 | 3.1 | 96.8 | 0.1 | 190 | below −20 |
| 5 | 5,7,7-trimethyl-2-(1,3,3-trimethylbutyl)octanoic acid | Hexadecanoic acid | 97.0 | 3.4 | 96.5 | 0.1 | 216 | −10.5 |
| 6 | 5,7,7-trimethyl-2-(1,3,3-trimethylbutyl)octanoic acid | Tetradecanoic acid | 94.8 | 4.0 | 95.8 | 0.2 | 285 | −17.0 |
| (1) | 2-heptylundecanoic acid | Octadecanoic acid | 94.1 | 2.8 | 97.1 | 0.1 | 530 | 12 |
| (2) | 2-ethylhexanoic acid | Octanoic acid | 90.3 | 11.1 | 88.5 | 0.4 | 52 | below −20 |

EXAMPLE 7

Skin Cream

| | |
|---|---|
| Stearic acid | 2.0 wt % |
| Stearyl alcohol | 6.0 |
| Reduced lanolin | 2.0 |
| Liquid oil preparation | 10.0 |
| Polyoxyethylene (25) cetyl ether | 3.0 |
| Glycerin monostearate | 2.0 |
| Propylene glycol | 6.0 |
| Purified water | 69.0 |
| Perfume | q.s. |

The liquid oil preparation in the above formulation is diacylglycerin obtained in Examples 1 to 5 and Comparative Example 1. The skin creams containing any of liquid oil preparations obtained in Examples 1 to 5 were stable and gave a refreshing feel. By contrast, the skin cream containing a liquid oil preparation obtained in Comparative Example 1 was poor in stability and gave a sticky feel.

EXAMPLE 8

Liquid Cream

| | |
|---|---|
| Liquid oil preparation | 30.0 wt % |
| Crystalline wax | 1.0 |
| Yellow wax | 4.0 |
| Sorbitan sesquioleate ester | 4.0 |
| Polyoxyethylene (20) sorbitan monooleate ester | 1.0 |
| Glycerin | 8.0 |
| Purified water | 52.0 |
| Perfume | q.s. |

The liquid oil preparation in the above formulation is diacylglycerin obtained in Examples 1 to 5 and Comparative Example 2. The liquid creams containing any of liquid oil preparations obtained in Examples 1 to 5 were stable and gave a refreshing feel and a smooth feel. By contrast, the liquid cream containing a liquid oil preparation obtained in Comparative Example 2 gave a slight smell of decomposition and an irritating feel.

EXAMPLE 9

Beauty Lotion

A beauty lotion of the following formulation was prepared in the usual manner.

| | |
|---|---|
| Diacylglycerin (Example 1) | 10 wt % |
| Ethanol | 60 |
| Glycerin | 5 |
| Pantothenyl ethyl ether | 0.1 |
| Vitamin E acetate | 0.05 |
| Water | balance |

This beauty lotion gave a good feel and produced a lasting moisturizing effect when applied to the skin.

EXAMPLE 10

Hair Tonic

A hair tonic of the following formulation was prepared in the usual manner.

| | |
|---|---|
| Diacylglycerin (Example 2) | 3 wt % |
| l-Menthol | 1 |
| 1,3-butanediol | 5 |
| Ethanol | 20 |
| Isopropanol | 40 |
| Water | balance |

This hair tonic gave a good feel but did not give a glossy appearance to the hair when applied to the hair.

EXAMPLE 11

Hair Care Lotion

A hair care lotion of the following formulation was prepared in the usual manner.

| | |
|---|---|
| Diacylglycerin (Example 3) | 15.0 wt % |
| Minoxidil | 0.5 |
| Ethinylestradiol | 5 |
| Pantothenyl ethyl ether | 0.05 |
| Benzyl alcohol | 5.0 |
| Isopropanol | 20.0 |
| 1,3-butanediol | 10.0 |
| Ethanol | 40.0 |
| Water | balance |

This hair care lotion did not a sticky feel to the scalp, nor did it give a glossy appearance to the hair.

EXAMPLE 12

After-Shave Lotion

An after-shave lotion of the following formulation was prepared in the usual manner.

| | |
|---|---|
| Glycerin | 1.0 wt % |
| Allantoin | 0.05 |
| Gaoben extract | 0.2 |
| l-Menthol | 0.1 |
| Persol MCX (UV light absorber) | 0.1 |
| Diacrylglycerin (Example 4) | 2.0 |
| Ethanol | 45.0 |
| Water | balance |

This after-shave lotion gave a cool feel and wet feel.

EXAMPLE 13

Toilet Lotion

A toilet lotion of the following formulation was prepared.

| | |
|---|---|
| Nicotinamide | 0.3 wt % |
| Glyerin | 5.0 |
| Diacylglycerin (Example 5) | 0.1 |
| Ethanol | 10.0 |
| Perfume | 0.02 |
| Methylparaben | 0.1 |
| Water | balance |

This toilet lotion gave a wet feel to the skin.

EXAMPLE 14

Sun Care Oil

A sun care oil of the following formulation was prepared in the usual manner.

| | |
|---|---|
| Diacylglycerin (Example 6) | 30 wt % |
| Olive oil | 10 |
| Octyldimethyl PABA | 8 |
| Persol 1789, tradename of Givaudan | 2 |
| Ethanol | 45 |
| Water | balance |

This sun care oil did not give a glossy appearance but produced a good sun screen effect.

EXAMPLE 15

White Peel-Off Type Pack

The product was obtained by adding 1,3-butanediol and glycerin in the below shown amounts to purified water and heating the mixture at 70°-80° C., adding thereto a mixture of the liquid oil preparation and polyoxyethylene-hardened castor oil, and stirring it well, gradually adding titanium oxide and then polyvinyl alcohol, dispersing them uniformly, cooling it down to about 35° C. and finally adding ethanol thereto.

| | (%) |
|---|---|
| Polyvinyl alcohol | 12 |
| Titanium oxide | 9 |
| Liquid oil preparation | 5 |
| (Examples 1-6 and Comparative Ex. 1, 2) | 5 |
| 1,3-butanediol | 2 |
| Glycerin | 3 |

| | (%) |
|---|---|
| Polyoxyethylene (20) hardened castor oil | 1 |
| Ethanol | 10 |
| Purified water | balance |

The pack including the liquid oil preparation of Comparative Example 1 is found to be more sticky on being peeled off than those of Example 1 to 6. The pack of Comparative Example 2 gave a glow on packing and offered a smell of decomposition on being peeled off.

Separately a cosmetic pack was prepared in the same manner as in Example 15 except using squalene for a liquid oil preparation.

The cosmetic packs were applied in an appropriate amount to the skin of the arm on the bending side of healthy persons. In 20 minutes, they were peeled off. Conductance of the skin was measured with a given interval, employing Inpedance Meter of IBS Co.

Inpedance Meter of IBS Co. Ltd. Results are shown in Table 2.

TABLE 2

| the liquid oil preparation in the pack | Conductance ($\mu\Omega$) | | | | |
|---|---|---|---|---|---|
| | 10 min | 1 hour | 2 hour | 4 hour | 8 hour |
| Example | | | | | |
| 1 | 53 | 32 | 26 | 19 | 9 |
| 2 | 60 | 38 | 22 | 18 | 10 |
| 3 | 58 | 39 | 22 | 19 | 10 |
| 4 | 59 | 37 | 21 | 18 | 10 |
| 5 | 62 | 39 | 23 | 19 | 10 |
| 6 | 64 | 40 | 24 | 20 | 11 |
| Squalene | 40 | 25 | 17 | 12 | 3 |

EXAMPLE 16

Semi-Transparent Peel-Off Type Pack

| | (%) |
|---|---|
| Polyvinyl alcohol | 15.0 |
| bee gum | 1.0 |
| Liquid oil preparation (Example 6) | 6.0 |
| Dipropylene glycol | 3.5 |
| Glycerin | 1.5 |
| Sorbitol | 1.0 |
| Polyoxyethylene sorbitan monolauric acid ester | 1.0 |
| Ethanol | 10.0 |
| Purified water | 61.0 |

Dipropylene glycol, glycerin and sobrbitol were added to purified water and the mixture was heated to 70 to 80 degree centigrade. Bee gum was added thereto and dispersed therein well. A mixture of the liquid oil preparation and polyoxyethylene sorbitan monolauric acid ester was added thereto, followed by stirring. Polyvinyl alcohol was gradually added. The mixture was cooled to 35 degree centigrade. Ethanol was added finally to obtain the pack.

EXAMPLE 17

Powder Pack

| | (%) |
|---|---|
| Caoline | 20.0 |
| Bengel | 10.0 |
| Talc | 10.0 |
| Liquid oil preparation (Example 1) | 3.0 |

-continued

|  | (%) |
|---|---|
| Glycerin | 5.0 |
| 1,3-butanediol | 3.0 |
| Polyoxyethylene-hardened castor oil | 1.0 |
| Purified water | 48.0 |

Glycerin and 1,3-butanediol were added to purified water. The mixture was heated to 70 to 80 degree centigrade. A mixture of the liquid oil preparation and polyoxyethylene-hardened castor oil was added, followed by stirring. Caoline, bengel and talc were gradually added and the mixture was kneaded well to obtain the pack.

EXAMPLE 18

Wash-Off Type Pack Paste

|  | (%) |
|---|---|
| bee gum | 6.0 |
| Cerisite | 6.0 |
| Zinc oxide | 10.0 |
| Liquid oil preparation (Example 3) | 5.0 |
| Glycerin | 3.0 |
| Propylene glycol | 2.0 |
| Polyoxyethylene hardened castol oil | 1.0 |
| Ethanol | 10.0 |
| Purified water | 57.0 |

Glycerin and propylene glycol were added to purified water and the mixture was heated to 70 to 80 degree centrigrade. A mixture of the liquid oil preparation and polyoxyethylene-hardened castor oil was added and polyoxyethylene-hardened castor oil was added, followed by stirring. Cerisite, zinc oxide and bee gum were gradually added and the mixture was stirred. Finally ethanol was added to obtain the pack.

EXAMPLE 19

White Peel-Off Type Pack

A pack of the following formulation was prepared and determined in view of the moistening effect in the same manner as in Example 15. Table 2 shows the result.

TABLE 2

|  | (%) | | |
|---|---|---|---|
|  | invention | control 1 | control 2 |
| Polyvinyl alcohol | 12 | 12 | 12 |
| Titanium oxide | 9 | 9 | 9 |
| Liquid oil preparation (Example 6) | 5 |  | 5 |
| Propylene glycol | 5 | 5 |  |
| POE (20) hardened castor oil | 1 | 1 | 1 |
| Ethanol | 10 | 10 | 10 |
| Purified water | balance | balance | balance |

TABLE 3

|  | Conductances (μΩ) | | | | |
|---|---|---|---|---|---|
|  | 10 minute | 1 hour | 2 hour | 4 hour | 8 hour |
| invention | 63 | 38 | 23 | 18 | 12 |
| control 1 | 49 | 30 | 17 | 12 | 5 |
| control 2 | 40 | 28 | 15 | 14 | 6 |

EXAMPLE 20

Lip Stick

A lipstick was obtained by uniformly mixing the following components with one another at 120° C., casting it into a mold and cooling down.

|  | (%) |
|---|---|
| Ceresin | 5 |
| Polyethylene wax (average molucular wt. 850) | 8 |
| Microcrystalline wax | 5 |
| Candelilla wax glycol | 2 |
| Yellow wax | 5 |
| Liquid paraffin | 10 |
| oil of hohoba | 10 |
| Liquid oil preparation (Example 1-6, Comparative Ex. 1, 2) | 40 |
| Castor oil | 5 |
| Titanium oxide | 2 |
| Red colorant No. 204 | 1 |
| Yellow colorant No. 4 alminum lake | 3 |
| UV light absorbers (Parsol MCX) | 4 |

The lipsticks containing the liquid oil preparations obtained in Examples 1-6 were found to be superior in its spreadability, smoothness, a low stickness, and feeling of moisture, to that of Comparative Example 1, and then in no feeling of irritation and no bad smell to that of Comparative Example 2.

EXAMPLE 21

Lip Cream

The following ingredients were mixed uniformly with one another at 120° C., cased into a mold and cooled down to form a lip cream.

|  | (%) |
|---|---|
| Ceresin | 10 |
| Microcrystalline wax | 3 |
| Polyethylene wax (average molecular weight of 1000) | 5 |
| Carnauba wax | 4 |
| Liquid paraffin | 10 |
| Liquid oil preparation (Examples 1-6, Comp. Examples 1, 2) | 15 50 |
| UV light absorbers (Parsol 1789) | 3 |

The lip creams containing the liquid oil preparations obtained in Example 1-6 were found to be superior in its spreadability, smoothness, a low stickness, feeling of moisture, to that of Comparative Example 1, and then in no feeling of irritation and no bad smell to that of Comparative Example 2.

EXAMPLE 22

Cream

|  | (%) |
|---|---|
| <oil phase> |  |
| Stearic acid | 2 |
| Cethanol | 1 |
| Colesterol | 1 |
| Squalene | 10 |
| liquid oil preparation (Examples 1-6 and Comp. Example 1, 2) | 20 |
| POE (40) hardened castor oil | 0.5 |
| Monostearic acid sorbitan | 2.0 |
| Butylparaben | 0.1 |
| <aqueous phase> |  |

-continued

| | (%) |
|---|---|
| Methylparaben | 0.2 |
| Glycerin | 10 |
| 1,3-Butylglycol | 5 |
| Perfume | 0.1 |
| Potassium hydroxide | 0.1 |
| Water | balance |

A cream was prepared from the above shown oil phase and aqueous phase by the following method.

Preparation Method

The ingredients of the aqueous phase were mixed with one another and dissolved with heat at 70° C. The ingredients of the oil phase were mixed with one another and heated at 70 degree centigrade. The oil phase was added to the aqueous phase and the mixture was emulsified with an emulsifier. The emulsion was cooled down to 30° C. with a heat-exchanger A cream was obtained by filling.

The creams containing the liquid oil preparations obtained in Examples 1-6 were found to be low in stickiness and glossiness and have feeling of smoothness, compared with Comparative Example 1. It did not smell bad, nor did it give any feeling of irritation. The cream containing the liquid oil preparation obtained in Comparative Example 2 was found to have smell of decomposition and give feeling of irritation (hot feeling) to the skin.

EXAMPLE 23

Liquid Cream

| | (%) |
|---|---|
| <oil phase> | |
| Cethanol | 1 |
| Olive oil | 3 |
| oil of hohoba | 2 |
| liquid oil preparation | 20 |
| (Examples 1-6 and Comp. Example 1, 2) | |
| Polyoxyethylene (10) hardened caster oil | 1 |
| Monostearic acid sorbitan | 1 |
| Butylparaben | 0.1 |
| <Water phase> | |
| Methylparaben | 0.1 |
| Glycerin | 2 |
| 1,3-Butylglycol | 2 |
| Ethanol | 3 |
| perfume | 0.1 |
| water | balance |

An emulsion was prepared from the oil phase and aqueous phase in the same manner as in Example 22. The emulsions containing the liquid oil preparations obtained in Examples 1-6 were found to be low in stickiness and glossiness and offer feeling in touch of smoothness, no feeling of irritation and no bad smell, in comparison with Comparative Example 1. The emulsion from Comparative Example 2 offered a bad smell and gave feeling of hot irritation to the skin.

EXAMPLE 24

Semi-Transparent Cosmetic

| <Components> | (%) |
|---|---|

-continued

| | (%) |
|---|---|
| (1) Liquid oil preparation in Examples 1-6 | 0.2-10 |
| (2) Dipropylene glycol | 5.0 |
| (3) Glycerin | 10.0 |
| (4) Polyethylene glycol | 1.0 |
| (5) POE (40) hardened castor oil | 2.5 |
| (6) Butylparaben | 0.1 |
| (7) Methlyparaben | 0.3 |
| (8) Perfume | 0.1 |
| (9) Water | balance |

Method for Production

The ingredients 1)-6) and 8) were mixed together and dissolved by heating, kept at 50° C. To the mixture, 7 and 9) were separately dissolved together by heating at 70 ° C. and they were gradually added. They were emulsified and cooled down to room temperature to obtain a cosmetic. The products comprising the respective liquid oil preparations obtained in Examples 1-6 in amounts of 1.0, 1.5 and 2.5% were observed to be translucent. That of 0.2% was transparent and that of 10% was milky or was involved in separation into two phases.

We claim:

1. A diacylglycerin having the formula (I):

wherein two of $R_1$, $R_2$, and $R_3$ independently are (a) a residue of a straight-chain saturated fatty acid having 11-13, 15-17 carbon atoms, and (b) a residue of a branched-chain saturated fatty acid having 10-18 carbon atoms, and the third of $R_1$, $R_2$ and $R_3$ is a hydrogen atom, with the proviso that $R_1$, $R_2$ or $R_3$ is not a residue of a branched-chain saturated fatty acid represented by the formulas (i) to (iii):

(i) a residue of a methyl-branched isostearic acid represented by the formula;

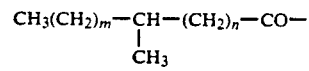

wherein m and n each are integers of 4 to 10, and $m+n=14$, distributed with the center at $m=n=7$;

(ii) a residue of 5,7,7-trimethyl-2-(1,3,3-trimethyl-butyl)-octanoic acid; or (iii) a residue of 2-heptylundecanoic acid.

2. A liquid oil composition comprising (A) the diacylglycerin (I) as defined in claim 1 and (B) another oil liquid.

3. A liquid cosmetic composition comprising (A) the diacylglycerin having formula (I'), (B) a lower alcohol and (C) water

wherein two of $R_1$, $R_2$, and $R_3$ both independently are (a) a residue of a straight-chain saturated fatty acid having 11-17 carbon atoms, and a residue of a branched-chain saturated fatty acid having 10-18 carbon atoms, and the third of $R_1$, $R_2$, or $R_3$ is a hydrogen atom.

4. A cosmetic pack composition comprising
    (A) the diacylglycerin having the formula (I') according to claim 3 and
    (B) a cosmetically acceptable carrier.

5. An oily solid cosmetic composition comprising
    (A) the diacylglycerin having the formula (I) according to claim 3 and
    (B) a hydrocarbon wax.

6. An emulsion cosmetic composition comprising
    (A) the diacylglycerin having the formula (I) according to claim 3,
    (B) a surfactant and
    (C) water.

* * * * *